United States Patent [19]

Hudson et al.

[11] 4,117,241

[45] Sep. 26, 1978

[54] POLYMERIZABLE MATERIALS

[75] Inventors: Alan George Hudson, Maidstone; Alec Richard Hornsey Tawn, Orpington, both of England

[73] Assignee: Coates Brothers & Co., Ltd., London, England

[21] Appl. No.: 552,329

[22] Filed: Feb. 24, 1975

Related U.S. Application Data

[63] Continuation-in-part of Ser. No. 322,938, Jan. 12, 1973, abandoned.

[30] Foreign Application Priority Data

May 19, 1972 [GB] United Kingdom ............... 23757/72

[51] Int. Cl.² ............................................. C07C 69/54
[52] U.S. Cl. ..................................... 560/224; 560/205
[58] Field of Search ..................... 260/486 R, 482 R; 560/224, 204

[56] References Cited

U.S. PATENT DOCUMENTS 3,163,623  12/1964  Sekmakas ................................ 260/72
3,230,275  1/1966   Sekmakas ............................... 260/873
3,318,971  5/1967   Chloupek et al. .................... 260/826

Primary Examiner—Paul J. Killos
Attorney, Agent, or Firm—Marn & Jangarathis

[57] ABSTRACT

A polymerizable material is formed by the reaction of: (A) acrylamide or methacrylamide; (B) from 1.5 to 2 moles, per mole of acrylamide or methacrylamide, of formaldehyde; and (C) an amount equivalent to the formaldehyde of a hydroxyl-group containing component comprising one or more hydroxyl or group-containing compounds containing from 1 to 4 primary or secondary hydroxyl groups per molecule, at least one of the hydroxyl groups-containing compounds being a monoacrylate or monomethacrylate of a diprimary, disecondary or primary-secondary diol, the said monoacrylate or monomethacrylate being used in an amount of from 0.1 to $k$ mole, per mole of acrylamide or methacrylamide, when the average number of hydroxyl groups per molecule of the hydroxyl group-containing component is 1 and in an amount of from 0.95 to $k$ mole, per mole of acrylamide or methacrylamide, when the average number of hydroxyl groups per molecule of the hydroxyl group-containing component is greater than 1, $k$ being the number of molecules of formaldehyde reacted per mole of acrylamide or methacrylamide.

14 Claims, No Drawings

POLYMERIZABLE MATERIALS

This application is a continuation-in-part of U.S. Application Ser. No. 322938 filed on Jan. 12, 1973, now abandoned This invention is concerned with improvements in and relating to polymerisable materials and the preparation and use thereof. More particularly, the invention is concerned with substantially monomeric polymerisable materials which may be used as one or the only ingredient of a polymerizable composition such as a surface coating composition, impregnant composition, laminant composition or adhesive composition.

Substantially monomeric polymerizable material containing the acrylic or methacrylic moiety:

$$CH_2 = C(X)CO -$$

(in which X is a hydrogen atom or a methyl group) are well known and examples of such materials include acrylic acid and methacrylic acid themselves; their esters for example methyl methacrylate, ethylene glycol dimethacrylate, trimethylolpropane triacrylate and hydroxyethyl acrylate; and their unsubstituted and N-substituted amides, for example acrylamide, methacrylamide, N-hydroxymethyl acrylamide, N-butyl methacrylamide and N-(1,1-dimethyl-3-oxobutyl) acrylamide.

These materials may be polymerized or copolymerized using a free radical initiator (e.g. a peroxide) or by exposure to ionizing radiation or ultra violet light. However, few of the known acrylic or methacrylic monomers may be readily and efficiently polymerized alone, in the form of thin films, by exposure to ultra violet light or ionizing radication and their use may be further restricted by such factors as volatility, viscosity and cost. Further, the amides are generally solid at ambient temperatures and have only limited solubility in or compatibility with many of the solvents, monomers and polymers commonly used in the formulation of surface coatings, impregnants, laminants and adhesives.

In order to overcome the disadvantages of these known acrylic monomers, it has been common practice to use the monomeric acrylate or methacrylate esters in conjunction with polymers (which may or may not be unsaturated). Thus, for example, the simple alkyl acrylates or methacrylates do not polymerize sufficiently rapidly when exposed to ultra violet light or ionizing radiation unless they have a proportion of dissolved polymer and such a solution may then be too viscous for application by conventional methods. The triacrylates of trihydric alcohols polymerize somewhat more rapidly but are poor solvents and it is, thus, difficult to formulate products from them having the necessary balance of application characteristics, film properties and cost.

According to the invention there is provided a process for the preparation of substantially monomeric polymerizable materials, which are generally liquids at temperatures of from 15° to 30° C and which may be polymerized thermally or by exposure to ultra violet light or high energy radiation which comprises reacting together, in one or more stages and in the presence of a polymerization inhibitor, (A) acrylamide or methacrylamide; (B) at least 1.5 moles, per mole of acrylamide or methacrylamide, of formaldehyde; and (C) a hydroxyl group-containing component comprising one or more hydroxyl group-containing compounds containing from 1 to 4 primary or secondary hydroxyl groups per molecule, at least one of the hydroxyl group-containing compounds being a monoacrylate or monomethacrylate of a diprimary diol, disecondary diol or primary-secondary diol, the said hydroxyl group-containing component being used in an amount equivalent to the formaldehyde up to 2 moles of formaldehyde; the said monoacrylate or methacrylate being used in an amount of from 0.1 to $k$ mole, per mole of acrylamide or methacrylamide, when the average number of hydroxyl groups per molecule of the hydroxyl group-containing component is 1 and in an amount of from 0.95 to $k$ mole, per mole of acrylamide or methacrylamide, when the average number of hydroxyl groups per molecule of the hydroxyl group-containing component is greater than 1, $k$ being the number of moles of formaldehyde reacted per mole of acrylamide or methacrylamide.

Preferably, the said monoacrylate or monomethacrylate is employed in an amount of from 0.95 to 1 mole, per mole of acrylamide or methacrylamide, regardless of the average number of hydroxyl groups per molecule of the hydroxyl group-containing component.

It is generally preferred that from 1.9 to 2 moles of formaldehyde be used, per mole of acrylamide or methacrylamide, since it has been found that amounts of formaldehyde below this range may (depending upon the nature of the hydroxyl group-containing component) lead to a product containing excessive amounts of precipitated solid necessitating either filtration (with its attendant losses and increased costs) or re-solution of the precipitate by dilution of the composition with a solvent containing vinyl or vinylidene groups such as styrene or an acrylate or methacrylate ester. Although it is possible to use such a solvent diluent in the compositions of this invention, it is often preferred not to do so.

As stated above, the hydroxyl group-containing component (C) may comprise a mixture of hydroxyl group-containing compounds and may be thus regarded as comprising two components (C') a monoacrylate or monomethacrylate of a diprimary diol, a disecondary diol or a primarysecondary diol; and (D) one or more hydroxyl group-containing monomers (other than the said monoacrylate or monomethacrylate) containing from 1 to 4 primary or secondary hydroxyl groups.

In the following description reference will generally be made to the materials of the invention and preparation thereof wherein the hydroxy-group containing component (C) comprises two components, namely the monoacrylate or monomethacrylate (C') and the other hydroxyl group-containing compounds(s) (D). It will be appreciated that, in general, all the comments below will apply to those compositions wherein components (C) consists only of (C'), the monoacrylate or monomethacrylate.

The process may be carried out in one stage (as is generally preferred for economic reasons) or it may be carried out in several stages. Thus, for example, part of the formaldehyde may be introduced as a pre-formed formal of the hydroxyl group-containing compound D or as the N-methylol amide.

The amount and nature of the ingredients used in forming any particular material in accordance with the invention will depend upon the intended end use of the material. In general, however, it may be said that products which will contain large numbers of vinylic or vinylidene double bonds in the molecule tend to cure more rapidly and to yield end products of greater rigidity than compounds containing smaller numbers of the said double bonds. Similarly, compositions or materials having a relatively high content of long alkyl, alkenyl or alkoxy chains tend to be relatively soft and flexible and a high content of polar groups, provided for example by the use of a polyalkylene glycol as component D, will tend to lower the resistance of the cured article to water. It will thus be clear that the purpose of any particular composition can be modified and chosen by selecting the appropriate nature of the ingredients, especially ingredients (C') and (D), the nature of ingredients (A) and (B) being fixed. Component B, the formaldehyde, is preferably, as stated above, used in the form of paraform although, for example an aqueous solution of formaldehyde may be used although the use of this would involve the removal, by distillation, of additional water.

Examples of component (C'), i.e. the hydroxyl group-containing monoacrylate or monomethacrylate include hydroxyethyl acrylate, hydroxyethyl methacrylate, 2-hydroxypropyl acrylate, 2-hydroxypropyl methacrylate, 3-hydroxypropyl acrylate, 3-hydroxypropyl methacrylate, 4-hydroxybutyl acrylate, 4-hydroxybutyl methacrylate, 2-hydroxybutyl acrylate, 2-hydroxybutyl methacrylate, 3-hydroxybutyl acrylate, 3-hydroxybutyl methacrylate, 3-hydroxy-2-methylpropyl acrylate, 3-hydroxy-2-methylpropyl methacrylate, 2-hydroxyoctyl acrylate, 2-hydroxyoctyl methacrylate, 3-oxa-5-hydroxypentyl acrylate, 3-oxa-5-hydroxypentyl methacrylate, 3-thia-5-hydroxypentyl acrylate and 3-thia 5-hydroxypentyl methacrylate. In general, the acrylates are preferred to the methacrylates and it is often preferred to use compounds containing primary hydroxy groups rather than those containing secondary hydroxy groups because the former react rather more rapidly than the latter.

The hydroxyl group-containing compound(s) (D) preferably have melting points below about 25° C, however compounds having melting points above 25° C may be used in admixture with those having melting points below 25° C, provided that the whole mixture melts below about 25° C. Thus, in general, unless the melting point of component (D) is below about 25° C, the products tend to be solid or to contain solid matter in suspension, necessitating dilution of the composition with a solvent containing vinyl or vinylidene groups or, where there is solid matter in suspension, removal of the suspended solid matter by filtration. It should be noted, however, that both trimethylol propane and pentaerythritol, which have melting points above 25° C, give products which do not suffer from the above defects. A wide variety of hydroxyl group-containing compounds may be used as component (D) and may, for convenience, be divided into five classes; namely, monohydric compounds, dihydric compounds, trihydric compounds, tetrahydric compounds and mixtures of different compounds. The various classes and examples thereof are discussed below.

Monohydric compounds

1a. Aliphatic monohydric primary or secondary alcohols of the general formula $C_mH_{2m+1}OH$ where m is from about 4 to 12. Alcohols having m = 2 or 3 can be used but their volatility necessitates the use of special preparative techniques which are inconvenient and relatively costly. Typical examples of suitable aliphatic monohydric alcohols are n-butanol, isobutanol, n-pentanol, n-octanol, 2-ethylhexanol, 3,5,5-trimethyl-hexan-1-ol and n-decanol.
1b. Cyclic alcohols such as cyclohexanol, the methyl cyclohexanols the dimethyl cyclohexanols, benzyl alcohol and 2-phenyl ethanol.
1c. Aliphatic monounsaturated primary and secondary monohydric alcohols of the general formula $C_{m'}H_{2m'-1}OH$ where m' is from 3 to about 18, such as allyl alcohol, methallyl alcohol, undec-10-en-1-ol and oleyl alcohol.
1d. Unsaturated fatty alcohols such as linoleyl alcohol and linolenyl alcohol.
1e. Hydroxylalkyl esters of saturated or unsaturated aliphatic mono- carboxylic acids and hydroxyalkyl esters of the general type $R^1OOC . R^2 . COOR^3$ where $OOC . R^2COO$ is the residue of an aliphatic or alicyclic dicarboxylic acid, $R^1$ is an alkyl or alkenyl group and $R^3$ is a hydroxyalkyl group; for example 4-hydroxybutyl propionate, 2-hydroxyethyl oleate, 3-hydroxypropyl crotonate n-butyl hydroxyethyl maleate and n-amyl hydroxyethyl tetrahydrophthalate.
1f. Monoalkyl and monoalkenyl ethers of dihydric alcohols such as 2-ethoxy ethanol, 2-butoxy ethanol, 2-allyloxy propan-l-ol, 3-oxa-pentan-1-ol and 3-oxa-heptan-l-ol.
1g. Dialkyl and dialkenyl ethers of trihydric alcohols, and trialkyl and trialkenyl ethers of tetrahydric alchols, such as trimethylol propane diallyl ether, pentaerythritol triallyl ether and pentaerythritol ether.
1h. The diesters of trihydric alcohols and the triesters of tetrahydric alcohols with saturated or unsaturated aliphatic carboxylic acids such as glycerol dictrotonate, trimethylol-propane dicaprylate and pentoerythritol trioleate.
1i. Alkyl and cycloalkyl esters of hydroxy acids such as 2-ethylhexyl glycollate, n-butyl lactate and cyclohexyl ricinoleate.

Dihydric compounds

Aliphatic and acicylclic saturated and unsaturated dihydric primary or secondary alcohols such as ethanediol, 1,2-propane diol, 1,3-propane diol, 1,3-butane diol, 1,4-butane diol, 2-butane-1,4-diol and 2,2-bis(4-hydroxycyclohexyl)propane.

It may be noted that many members of this class containing more than about 4 carbon atoms have melting points above about 25° C. but may be employed in admixture with other compounds as described above to give a mixture melting below about 25° C.

2b. Polyalkylene glycols of the formula $H(OCH_2CH)_{m''}OH$
   $\qquad\qquad\qquad\qquad\qquad\qquad\quad |$
   $\qquad\qquad\qquad\qquad\qquad\qquad\quad R^4$
where $R^4$ is H or $CH_3$ and m" is at least 2 and preferably not more than 4, such as diethylene glycol, triethylene glycol, dipropylene glycol and tripropylene glycol.
2c. 3-Thia-pentan-1,5-diol.
2d. Monoesters of trihydric alcohols with saturated or unsaturated aliphatic carboxylic acids; such as glyceryl-1-monocaproate, glyceryl-1-monooleate, trimethylolpropane monocaprylate and trimethylolethane monolinoleate.
2e. Monoalkyl and monoalkenyl ethers of trihydric alcohols such as glyceryl-1-allyl ether, trimethylol propane allyl ether, trimethylol ethane mono oleyl ether, glyceryl-1-hexyl ether and 1-methoxy butane-2,3-diol.
2f. Di(hydroxy alkyl) esters of dicarboxylic acids such as di-(hydroxypropyl) itaconate, di-(hydroxyethyl) maleate and di-(hydroxybutyl) adipate. This class includes compounds of the structure:

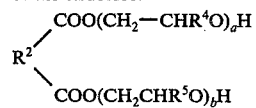

where $R^2$ is the hydrocarbon moiety of the dicarboxylic acid, $R^4$ and $R^5$ are H or $CH_3$ and (a + b) lies in the approximate range 4–20. Such compounds are conveniently prepared by the reaction of the dicarboxylic acid with ethylene oxide and/or propylene oxide. A typical example is the reaction product of itaconic acid and propylene oxide in which $R^4$ and $R^5$ are $CH_3$, $R^2$ is -continued

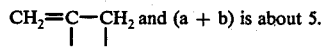
and (a + b) is about 5.

2g. The dialkyl and dialkenyl ethers of tetrahydric alcohols, such as pentaerythritol diallyl ether.
2h. The diesters of tetrahydric alcohols with saturated or unsaturated aliphatic carboxylic acids, such as erythritol di-2 ethyl hexoate and pentaerythritol dilinoleate.

Trihydric compounds

3a. Aliphatic trihydric primary or secondary alcohols such as glycerol, the butane triols, the hexane triols and trimethylol propane.
3b. Monoesters of tetrahydric alcohols with saturated or unsaturated aliphatic carboxylic acids. Most of these have melting points above about 25° C. and are best employed as mixtures as described above.
3c. Monoalkyl and monoalkenyl ethers of tetrahydric alcohols. Most have melting points above about 25° C. and are best employed as mixtures as described above.

Tetrahydric compounds

4. Most commercially available tetrahydric alcohols have melting points above about 25° C, except diglycerol, but, notwithstanding its high melting point, pentaerythritol does yield liquid products. In general, it is preferred to use these materials in the form of mixtures.

Mixtures

Mixtures of the hydroxyl group-containing compounds may be used for reasons of economy or because it is desired to employ compounds which when used alone would yield solid products. Typical mixtures used for reasons of economy are the fatty alcohols produced from the mixed acids occurring in natural oils and fat (e.g. the so-called palm kernel alcohols), the products of alcoholysis of soya bean oil with trimethylol propane) and the mixture of partial esters formed by the esterification of a polyhydric alcohol with less than the stoichiometric equivalent of a carboxylic acid or mixture of carboxylic acids.
Typical compounds melting above about 25° C and which tend to yield solid products or products containing much solid matter in suspension are n-tetradecanol, neopentyl glycol, and glycerol monopalmitate. These are readily incorporated in the form of mixtures such as equimolar mixtures of n-tetradecanol with n-octanol, neopentyl glycol and diethylene glycol, and glycerol monopalmitate with glycerol monolinoleate, all of which mixtures give acceptable yields of liquid products.

The reaction between the components (A), (B), (C') and (D) may, as stated above, be carried out in one or more stages. Whenever the components being condensed contain vinyl or vinylidene unsaturation (i.e. in all cases except that stage of a multistage process which comprises condensation of B with a non-vinyl or non-vinylidene component (D) it is necessary to carry out the reaction in the presence of a free radical polymerization inhibitor such as hydroquinone in order, to prevent any significant amount of polymerization during the condensation and to ensure that the product is substantially monomeric. As a further precaution against premature polymerization and to prevent discolouration, the reaction is suitably carried out under an atmosphere of an inert gas such as nitrogen.

The materials may be simply prepared merely by heating together components (A), (B), (C') and (D) in the desired quantities in the presence of a free radical polymerization inhibitor at a temperature and pressure such that the water of reaction distils freely from the mixture. Thus the reaction may conveniently be carried out at a temperature of about 130° C at atmospheric or slightly sub-atmospheric pressure.

A convenient procedure for practising the process of the invention is carried out as follows using a reaction vessel equipped with a stirrer, thermometer and Dean and Stark separator.

A quantity of an inert solvent, for example toluene, is charged to the reaction vessel together with components (C') and (D), and the mixture is then heated to about 80° C at which temperature component (A) is added. The temperature of the mixture is then raised to about 90° C and component (B), in the form of paraform, is added thereto. The temperature of the reaction mixture is then raised until the evolution of water commences and the reaction mixture is maintained under reflux until no further water is collected in the Dean and Stark separator; this point is normally reached before the temperature of the reaction mixture exceeds 145° C. Reduced pressure is then applied to the flask and the inert solvent is distilled off leaving the material of the invention as a still residue which is then discharged and allowed to cool. If the residue contains solid matter in suspension, this may be either removed by filtration or dissolved by the addition of a solvent containing vinyl or vinylidene unsaturation.

The preferred inert solvent for use in the process as described above is toluene because it permits refluxing at a temperature which, in the presence of a suitable inhibitor, does not provoke premature polymerization and also because it is easily removed by vacuum distillation and is a generally satisfactory solvent for the reactants and products. However, other inert solvents such as xylene may also be used. If component (D) is substantially immiscible with water, yields an azeotrope with water distilling at from about 90° C to about 140° C and, in the quantity used, permits removal of substantially all of the water of reaction at a reactant temperature below 145° C, then component (D) may itself be used as reaction solvent. Generally, in such a case, component (D) will be used in excess and the excess subsequently removed. An example of such a component (D) is n-butanol.

As stated above, the polymerizable materials of the invention may be used as ingredients of polymerizable compositions such as varnishes, laminants, impregnants and adhesives and, preferably, form the sole or principal ingredient of such compositions. However, in order to give the compositions the optimum application properties, the materials of the invention may be thinned by the addition of monomers containing vinyl or vinylidene unsaturation or may be thickened by dissolving in them polymeric materials (either saturated or unsaturated) of known type. If it is desired to produce a coloured product, the composition may be pigmented with conventional additives to give paints or printing inks. The compositions comprising the polymerizable materials of the invention may be cured by thermal means or by irradiation with ultra violet or ionizing radiation. If the composition is intended for thermal cure, it should contain a free radical initiator such as a peroxide, or, alternatively, the application conditions should be so arranged that the composition comes into contact with a free radical initiator before curing, for example by pre-treating the substrate with the free radical initiator. Where the compositions are intended for cure by ultra violet light, they should contain an ultra violet sensitizer. Where the compositions are intended for curing by means of ionizing radiation, such as an electron beam, no initiator or sensitizer is required.

In order that the invention may be well understood, the following Examples are given by way of illustration. In the Examples the apparatus used comprised a multi-necked flask, heated by an electric mantle, and equipped with a stirrer, nitrogen inlet, thermometer dipping in the reaction mixture and a Dean & Stark separator communicating with a water cooled condenser. After completion of the reaction the Dean & Stark separator was replaced by a distillation set and a receiver communicating with a vacuum pump. The paraformaldehyde used in examples 1 –28 uses an 87% HCHO paraformaldehyde.

EXAMPLE 1

37 ml toluene, 0.2g hydroquinone and 1 mole of n-butanol were placed in the reaction flask and heated to 80° C. whereupon 1 mole of hydroxyethyl acrylate was added thereto. The temperature was again raised to 80° C. and 1 mol of acrylamide was added thereto. The temperature was then raised to 90° C. and 2.13 moles of formaldehyde in the form of paraformaldehyde was added to the mixture. The mixture was then heated to reflux and water of reaction was removed by brisk reflux of toluene via the separator. As the temperature of the reaction mixture approached 140° C. evolution of water ceased. The processing solvent (toluene) was then removed by vacuum distillation at a batch temperature below 140° C. The product remaining in the flask was allowed to cool and was then filtered. The filtrate was a composition of the invention in the form of a clear liquid having a viscosity of 0.3 stokes at 25° C.

EXAMPLE 2

The procedure of Example 1 was repeated using 1 mole of 3,5,5-trimethyl hexanol-1 in place of the n-butanol. The product was a clear liquid having a viscosity of 0.6 stokes at 25° C.

EXAMPLES 3, 4 and 5

The procedure of Example 1 was repeated replacing the n-butanol respectively by 1 mole, of 3-oxa-heptanol-1, 1 mole of oleyl alcohol and 1 mole of cyclohexanol. In each case the product was a clear, oily liquid.

EXAMPLE 6

The procedure of Example 1 was repeated replacing the n-butanol with n-decanol. The product was a clear oily liquid, which precipitated some solid matter on standing.

EXAMPLE 7

The procedure of Example 1 was followed replacing the hydroxyethyl acrylate with 1 mole of hydroxyethyl methacrylate. The product was a clear oily liquid.

EXAMPLE 8

In this Example component D is hydroxyethyl acrylate and is identical with component C'.

37 ml toluene, 0.2g hydroquinone and 2 moles of hydroxyethyl acrylate were charged to the reaction flask and heated to 80° C. at which temperature 1 mol of acrylamide was added. The temperature was raised to 90° C and 2.13 moles of formaldehyde in the form of paraformaldehyde were added to the mixture. The temperature was raised to reflux and the rest of the process completed as in Example 1. The product was a clear liquid having a viscosity of 1 stoke at 25° C.

EXAMPLE 9

Example 8 was repeated except that 1 mole of methacrylamide was used in place of the acrylamide. The product was a clear oily liquid.

EXAMPLE 10

The reaction flask was charged with 60 ml toluene, 0.3g hydroquinone and 1 mole ethylene glycol, and heated to 80° C. whereupon 2 moles of hydroxyethyl acrylate were added. The mixture was reheated to 80° C. and 2 moles of acrylamide were added. The temperature was then raised to 90° C. and 4.26 moles of formaldehyde in the form of paraformaldehyde were added. The mixture was then heated to reflux and the process completed as in Example 1. Substantial quantities of solid matter were removed at the filtration stage but the filtrate was a clear, somewhat viscous liquid.

EXAMPLE 11

The reaction flask was charged with 75 ml toluene, 0.45g hydroquinone and 1 mole trimethylolpropane, heated to 80° C. and 3 moles hydroxyethyl acrylate were added thereto. The temperature was again raised to 80° C. and 3 moles acrylamide were added. The temperature was then raised to 90° C., 6.39 moles of formaldehyde were added in the form of paraformaldehyde after which the whole was raised to reflux and the process completed as in Example 1. The product was a clear liquid having a viscosity of 5 stokes at 25° C.

EXAMPLE 12

The reaction flask was charged with 25 ml toluene, 0.15g hydroquinone and 0.25 mole pentaerythritol, heated to 80° C. and 1 mol hydroxyethyl acrylate added thereto. After reheating to 80° C., 1 mole acrylamide was added. The mixture was then heated to 90° C., 2.13 mol of formaldehyde in the form of paraformaldehyde added, after which the whole was raised to reflux and the process completed as in Example 1. The product was a clear liquid having a viscosity of 8.6 stokes at 25° C.

Example 13

(a) Component D, a mixed ester containing on average 2 primary hydroxyl groups per mole, was first prepared as follows.

1 mole of trimethylolpropane was heated with 1 mole of "Acid 1098" at 250° C. under conditions of distillation in a stream of nitrogen until the acid value of the mixture had fallen to less than 5 mgKOH/g. "Acid 1098" is a commercially available mixture of fatty acids of average chain length about 9 carbon atoms comprising mainly those acids of 8, 9 and 10 carbon atoms chain length. The mean molecular weight of the sample used was found by alkali titration to be 153.

The resultant mixed ester was assumed to have a mean molecular weight of 269 and an average of 2 primary hydroxyl groups per mole.

(b) The mixed ester was used to prepare a composition according to the invention as follows.

The reaction flask was charged with 35 ml toluene, 0.4g hydroquinone and 1 mole of the ester, heated to 80° C. and 2 moles hydroxyethyl acrylate added. The mixture was reheated to 80° C. and 2 moles of acrylamide were added. The mixture was then heated to 90° C., 4.2 moles of formaldehyde as paraformaldehyde were added and the whole was heated to reflux. The process was completed according to Example 1. The produce was a clear, somewhat viscous oil.

EXAMPLE 14

An example of the use of 1.5 moles formaldehyde per mole of acrylamide with hydroxyethyl acrylate as both components C' and D.

The reaction flask was charged with 20 ml toluene, 0.17g hydroquinone and 1.5 moles of hydroxyethyl acrylate, heated to 80° C. and 1 mole acrylamide added. The mixture was heated to 90° C. 1.5 moles formaldehyde as paraformaldehyde added and the whole then raised to reflux. The process was completed as in Example 1. The product was a clear, somewhat viscous liquid.

EXAMPLE 15

The procedure of Example 10 was followed replacing the ethylene glycol with 1 mole of 3-thia-pentan-1,5-diol. When filtered free of precipitated solid, the product was a viscous oil.

EXAMPLE 16

The procedure of Example 10 was followed replacing the ethylene glycol with a mixture of ⅓ mole ethylene glycol, ⅓ mole diethylene glycol and ⅓ mole 1,3-propanediol. Much solid matter was again deposited but the quantity was significantly less than in Example 10. After filtration the product was a viscous oil.

EXAMPLE 17

The procedure of Example 8 was followed replacing the hydroxyethyl acrylate with 2 moles of 4-hydroxybutyl acrylate. The product was a clear oily liquid.

EXAMPLE 18

Use of 2-stage process.

The reaction flask was charged with 60 ml toluene 0.2g hydroquinone and 1 mole hydroxyethyl acrylate, heated to 80° C. and 1 mol acrylamide added. The mixture was heated to 90° C. and 1.1 mole of formaldehyde was added as paraformaldehyde. The whole was then raised to reflux and held at reflux until no more water distilled into the separator. The quantity collected was about 1 mole. The mixture was then cooled to 100° C. and a further 1.1 mole of formaldehyde, as paraform, was added together with butanol 1 mole plus 0.5 mole excess. The whole was again raised to reflux and a further 1 mole of water was removed via the separator by which time evolution of water had ceased and the temperature of the reaction mixture was 142° C. Processing solvent comprising the toluene and the excess butanol was then removed by vacuum distillation keeping the reaction mixture below 140° C. The product was filtered to yield a clear oily liquid.

Curing tests

The foregoing products were tested for curing performance under various conditions. Films of different thicknesses were applied by conventional means, typically a bar coater, to various substrates such as glass, tinplate, chipboard, aluminium, ABS plastic, wood and paper.

Electron beam cure was tested by passing the coated substrate in an atmosphere containing not more than 1% oxygen at a speed of 100 linear feet per minute beneath the window of an electron beam generator operating at 125 keV and 5mA beam current, which treated the target material at a rate of 90 m.rad/sec. One pass through the beam under these conditions resulted in the coating receiving a dose of 4.7 m.rad.

Films varying in thickness from about 5 microns to about 40 microns, applied to glass, tinplate, aluminium, ABS and chipboard, and comprising the unmodified products of Examples 1, 2, 3, 5, 7, 8, 9, 10, 11, 12, 14, 15, 16, 17, 18 were all cured after 1 pass. Films of thickness about 10 microns to about 40 microns and comprising the products of Examples 4 and 13 and the filtered suspension of Example 6 required two passes through the beam to effect cure.

Cure in ultraviolet light was tested by exposing applied films of the products containing 5% by weight of a U.V. sensitiser to the radiation from a Philips HTQ high pressure mercury lamp backed by an eliptical reflector. The tube was 3 inches long and was rated at 200 watts per linear inch. The distance from lamp to film was 1 inch. Various times of exposure could be arranged by means of a shutter but it was difficult to reliably measure exposure times less than 1 second although some films did obviously cure in less than 1 second. The sensitiser used was "Trigonal 14" (Registered Trade Mark) which is believed to be a benzoin derivative. This was dissolved in the product before application to the substrate.

The products of Examples 1, 2, 6 (filtered suspension) 7, 8, 9, 10, 11, 12, 13, 15, 16, 18 were tested in this way in the form of films 10 – 12 microns tick applied to glass, tinplate, aluminium and A.B.S. plastic. All were fully cured after 1 second's exposure. The products of Examples 11 and 12 were cured by less than 1 second's exposure but the minimum time needed could not be accurately determined by the method of test employed.

A 20 micron film of a 5% solution of Trigonal 14 in the product of Example 11 on a glass plate was found to cure on exposure to bright sunlight for 40 minutes.

EXAMPLE 19

A wood-filling composition was prepared by dispersing 32 parts by weight of micronised talc in a solution of 5 parts of Trigonal 14 in 63 parts of the product of Example 11. This composition was applied to chipboard by means of a doctor blade at a film thickness of 50 microns. The film was cured hard and could be sanded after 5 seconds' exposure to the U.V. lamp.

EXAMPLE 20

A printing ink vehicle was prepared by dissolving 38 parts by weight of Santolite MHP (a commercial toluene sulphonamide resin - Santolite is a Registered Trade Mark) in a mixture of the product of Example 3, 26 parts, Arochlor 5460 (a polychlorinated polyphenyl - Arochlor is a Registered Trade Mark) 17 parts, and triethanolamine 1 part. Trigonal 14, 5 parts, was dissolved in this vehicle and the whole was then pigmented with 13 parts of benzidene yellow to yield a printing ink. This ink was printed on art paper by means of a proofing press. The prints, the film thickness of which was approx. 2 microns, were cured by 1 second's exposure to the U.V. lamp. An otherwise similar ink in which the product of Example 3 was replaced by an inert solvent failed to cure under these conditions.

EXAMPLE 21

A clear wood varnish was prepared by dissolving 1.5 parts by weight of benzoyl peroxide in 98.5 parts of the product of Example 11. The varnish was applied to smooth panels of parana pine at a film thickness of 20 microns. The coated panels were heated by means of a 2 kW infra-red lamp placed 4 inches above the coated surface. Cure took place so rapidly that the film became disrupted and numerous blow-holes appeared. Cure to a satisfactory film took place in 30 seconds when the distance between lamp and film was increased to about 18 inches.

In a further series of tests Examples 22 to 28 the cure in ultra violet light was tested by exposing films of products containing 5% by weight to Trigonal 14 to the radiation from a Hanovia high pressure mercury lamp, rated at 200 watts per linear inch, 12 inches long and backed by a eliptical reflector.

The distance from the lamp to the film was 3½ inches. Samples were passed under the lamp on a continuous conveyor at 200 ft/minute. Variation in the exposure time required to cure the film was achieved by recycling the panel.

EXAMPLE 22

100g of the suspension of Example 6 was mixed with 50g of a 1:1 by weight mixture of styrene and acrylic acid to yield a clear solution to which was added 5% by weight of Trigonal 14. A film of this varnish cured by the procedure outlined above, yielded a hard film after about ⅛sec exposure.

A further 100g of this suspension was mixed with 50g of a 1:1 by weight mixture of styrene and hydroxyethyl acrylate. A film of this varnish cured to a hard film after about ⅛sec exposure.

EXAMPLE 23 the procedure of Example 1 was repeated using the following reactants

| Toluene | 37 ml |
|---|---|
| Hydroquinone | 0.2 grams |
| Hydroxethyl acrylate | 1 mole |
| Trimethylolpropane diallyl ether | 0.8 mole |
| Methacrylamide | 1 mole |
| Formaldehyde as paraform | 1.8 mole |

The product was a liquid which deposited some solid matter on standing. Filtration yielded a clear liquid to which was added 5% w/w of Trigonal 14. A film of this varnish cured under the UV lamp to a flexible film in about ½ sec.

EXAMPLE 24

(Preparation of a Component C)

(c) 980 grams of Cardura E (the glycidyl ester of a synthetic branched chain fatty acid - "Cardura" is a Registered Trade Mark) was heated to 135° C in a stream of nitrogen, and 5g of benzyldimethylamine (catalyst) and 2.8 of hydroquinone (polymerisation inhibitor) were added. Acrylic acid (328 g) was then run in at such a rate that the temperature was maintained at 135° C. The reaction was contiued until the acid value of the mixture had fallen to 22mg KOH/g. The product was a clear amber liquid of viscosity 1.95 stokes at 25° C.

(b) 13ml of toluene, 26ml of n-butanol and 0.1g of hydroquinone were placed in a reaction flask and heated to 80° C whereupon a solution of one hydroxy equivalent of the hydroxy monomer of (a) in 1 mole of n-butanol was added thereto. The temperature was again raised to 80° C and 1 mole of methacrylamide added thereto, the temperature was then raised to 90° C and 1.83 moles of formaldehyde in the form of paraformaldehyde was added to the mixture. The mixture was then heated to reflux and water of reaction was removed by brisk reflux of toluene via the separator. Heating was terminated when a batch temperature of 140° C was attained. The processing solvent (toluene and unreacted n-butanol) was then removed by vacuum distillation of a batch temperature below 140° C. The product remaining in the flask was allowed to cool 5% by weight of Trigonal 14 was added to the product. A thin film of this solution cured to a flexible film under the UV lamp in about ¼ sec.

EXAMPLE 25

37ml of toluene, 0.2g of hydroquinone 1 mole hydroxyethyl acrylate, 0.5 mole of n-butyl lactate and 0.25 mole of dipropylene glycol were placed in a reaction flask and heated to 80° C. 1 mole of acrylamide was added thereto, the temperature was raised to 90° C and 2.1 moles formaldehyde in the form of paraformaldehyde was added to the mixture. The mixture was then heated to reflux and water of reaction was removed by brisk reflux of toluene via the separator. As the temperature of the reaction mixture approached 140° C evolution of water ceased. The processing solvent (toluene) was then removed by vacuum distillation at a batch temperature below 140° C. The product remaining in the flask was allowed to cool and was then filtered through a nylon gauze.

5% by weight of Trigonal 14 was added to the filtrate. A film of this varnish cured under the UV lamp to a hard film in about 1/20 sec.

EXAMPLE 26

The procedure of Example 25 was repeated using

| Toluene | 30 mls |
|---|---|
| Hydroquinone | 0.1g |
| Hydroxyethyl acrylate | 1 mole |
| *Hydroxpropyl itaconate | 1 hydroxy equivalent |
| Acrylamide | 1 mole |
| Formaldhyde as Paraformaldehyde | 2.1 mole |

*(A commercially available impure material having a hydroxyl value of 410 mg KOH/g).

The product was a clear liquid to which was added 5% by weight of Trigonal 14. A film of this varnish cured under the UV lamp to a hard film is about 1/16 sec.

EXAMPLE 27

Preparation of component D (a) A mixed partial ester of pentaerythritol was prepared from

| Xylol | 25 mls. |
|---|---|
| Pentaerythritol | 1 mole |
| Caprylic acid | 1 mole |
| Crotonic acid | 1 mole |

The reactants were charged to a reaction vessel fitted with a stirrer, thermometer, heater and Dean and Stark distillation unit and heated to 225° C. Water of reaction was removed azeotropically. The reaction was continued at 225° C until an acid value of 8 mg KOH/g had been attained.

The product was a white inhomogeneous suspension.

(b) The procedure of Example 25 was repeated using

| Toluene | 37 mls |
|---|---|
| Hydroquinone | 0.2 g |
| Hydroxyethylacrylatec | 1 mole |
| Mixed Ester of (a) above | 1 Hydroxy equivalent |
| Acrylamide | 1 mole |
| Formaldehyde as a Paraformaldehyde | 2.1 mole |

The product was a clear liquid to which was added 5% by weight of Trigonal 14. A film of this varnish cured under the UV lamp to a hard film in about 1/40 sec.

EXAMPLE 28

Preparation of component D (a) A mixed partial ester of pentaerythritol was prepared from

| Linseed oil | 1 mole |
| --- | --- |
| Pentaerythritol | 1 mole |
| Lead Acetate | 0.25g |

The linseed oil was charged to a reaction vessel fitted with a stirrer, thermometer, heater and nitrogen atmosphere and heated to 100° C. The pentaerythritol and lead acetate were added thereto and the temperature raised to 240° C. This temperature was maintained until a 3:1 by weight mixture of industrial methylated spirit and the reaction mixture yielded a clear solution at room temperature.

(b) The procedure of Example 25 was repeated using the following:

| Toluene | 37 ml |
| --- | --- |
| Hydroquinone | 0.2g |
| Hydroxyethylacrylate | 1 mole |
| Alcoholysis product of Ex.29 | 1 hydroxyl equivalent |
| Acrylamide | 1 mole |
| Formaldehyde as paraformaldehyde | 2.1 mole |

The product was a liquid which deposited some solid matter on standing. Filtration yielded a clear liquid to which was added 5% by weight of Trigonal 14. A film of this varnish cured under the UV lamp to a flexible film in about 1/13 sec.

EXAMPLE 29

A copolymer was prepared from:

| Hydroxyethyl acrylate | 928 parts |
| --- | --- |
| Paraform (82% HCHO)* | 304 parts |
| Hydroquinone | 0.75 parts |
| Acrylamide | 284 parts |
| Toluene | 174 parts |

*Commercially known as 82 S prills (ex Synthite Ltd., of West Bromich).

The hydroxyethyl acrylate, paraformalde and hydroquinone were placed in a reaction flask fitted with a stirrer, thermometer and water cooled reflux condenser and heated to gentle reflux. (110°–115° C). The temperature was held at 110/115 until the reaction mixture was a clear solution (1 and ¾ hours). The temperature was lowered, to approximately 90° C and the acrylamide and toluene added. The reflux condenser was replaced by a Dean and Start entrainment distillation unit. The temperature was raised to reflux (115° ) at which temperature the evolution of water commenced. This water was removed by brisk reflux of the toluene via the separator. As the temperature of the reaction mixture approached 145° C the evolution of water ceased. The temperature was lowered to 130° C. The processing solvent was removed by vacuum distillation on the cool down. 171 parts of water was removed: approximately 143 parts of process solvent was recovered.

Cure in ultraviolet light was tested by exposing an applied film of the product, containing 5% by weight of Trigonal 14, to the radiation from a Union Carbide (Linde Division) PARS-102 Plasma Arc Radiation System (Laboratory/Quality Control Model)(Regulator setting 350 ± p.s.i.g., chamber pressure 140 p.s.i.g. Arc current 107 ± A. All parameters monitored for 2 minutes to allow the system to stabilise).

At a conveyor speed of 200 ft./minute the coating cured to a hard film in one pass.

We claim:

1. A process for the preparation of a polymerizable material which comprises reacting together in one or more stages and in the presence of a polymerization inhibitor (A) a member selected from the group consisting of acrylamide and methacrylamide; (B) at least 1.5 moles, per mole of acrylamide or methacrylamide, of formaldehyde; and (C) a hydroxyl compound in an amount equivalent to the formaldehyde up to 2 moles of formaldehyde, said hydroxyl compound being selected from the group consisting of (C') monoacrylates and monomethacrylates of diprimary, disecondary and diprimary-secondary diols and mixtures of (C') and (D) at least one hydroxyl compound having from 1 to 4 primary or secondary hydroxyl groups, said component (C') being used in component (C) in an amount of from 0.1 to $k$ mole, per mole of said acrylamide or methacrylamide when the average number of hydroxyl groups of component (C) is one and in an amount of from 0.95 to $k$ mole, per mole of said acrylamide or methacrylamide when the average number of hydroxyl groups of component (C) is greater than 1, $k$ being the number of molecules of formaldehyde used per mole of acrylamide or methacrylamide.

2. A process according to claim 1 which comprises heating together components (A), (B) and (C) in the desired quantities in the presence of a free radical polymerization inhibitor at a temperature and pressure such that the water of reaction distils freely from the mixture.

3. A process as claimed in claim 1 in which the process is carried out in the presence of an inert solvent.

4. A process according to claim 1 in which the said monoacrylate or monomethacrylate is used in an amount of from 0.95 to 1 mole, per mole of acrylamide or methacrylamide.

5. A process according to claim 1 in which the hydroxyl group-containing component (C) comprises a mixture of hydroxyl group-containing compounds comprising two components, namely (C') a monoacrylate or monomethacrylate of a diprimary, disecondary or primary-secondary diol; and (D) one or more hydroxyl group containing compounds other than the said monoacrylate or monomethacrylate containing an average of 3 primary or secondary hydroxyl groups per molecule, the material being derived from the reaction of components (A), (B), (C') and (D) in a molar ratio of about 1:2:2:1/3.

6. A process according to claim 1 in which component (C) comprises a monoacrylate containing primary hydroxyl groups.

7. A process according to claim 1 in which the hydroxyl group-containing component other than the monoacrylate or monomethacrylate has a melting point below 25° C.

8. A process according to claim 1 in which the hydroxyl group-containing component other than the monoacrylate or monomethacrylate is trimethylol propane or pentaerythritol.

9. A polymerisable material produced by the process of claim 1.

10. A polymerizable material produced by the process of claim 4.

11. A polymerizable material produced by the process of claim 5.

12. A polymerizable material produced by the process of claim 6.

13. A polymerizable material produced by the process of claim 7.

14. A polymerizable material produced by the process of claim 8.

* * * * *